United States Patent
Spano, Jr. et al.

(10) Patent No.: US 6,671,579 B2
(45) Date of Patent: Dec. 30, 2003

(54) OVERRIDE HAVING BUILT IN AUDIT TRAIL FOR MEDICATION DISPENSING AND ADMINISTERING SYSTEMS

(75) Inventors: Philip H. Spano, Jr., McKees Rocks, PA (US); Robert B. Meek, Jr., Pittsburgh, PA (US)

(73) Assignee: McKesson Automation, Inc., Pittsburgh, PA (US)

( * ) Notice: Subject to any disclaimer, the term of this patent is extended or adjusted under 35 U.S.C. 154(b) by 0 days.

(21) Appl. No.: 10/267,772

(22) Filed: Oct. 9, 2002

(65) Prior Publication Data

US 2003/0195655 A1 Oct. 16, 2003

Related U.S. Application Data (63) Continuation-in-part of application No. 10/124,045, filed on Apr. 16, 2002.

(51) Int. Cl.[7] .......................... G06F 17/00; G07F 11/00
(52) U.S. Cl. ...................... 700/236; 700/237; 700/240; 700/244; 221/2; 221/7
(58) Field of Search ................................ 700/236, 237, 700/240, 243, 244, 242; 221/2, 7

(56) References Cited

U.S. PATENT DOCUMENTS

| | | | |
|---|---|---|---|
| 5,314,243 A | * | 5/1994 | McDonald et al. ............ 221/2 |
| 5,346,297 A | | 9/1994 | Colson, Jr. et al. |
| 5,520,450 A | | 5/1996 | Colson, Jr. et al. |
| 5,597,995 A | | 1/1997 | Williams et al. |
| 5,745,366 A | | 4/1998 | Higham et al. |
| 5,805,455 A | | 9/1998 | Lipps |
| 5,805,456 A | | 9/1998 | Higham et al. |
| 5,905,653 A | | 5/1999 | Higham et al. |
| 6,003,006 A | * | 12/1999 | Colella et al. ............... 705/2 |
| 6,011,999 A | | 1/2000 | Holmes |
| 6,175,779 B1 | * | 1/2001 | Barrett ....................... 700/242 |
| 6,202,923 B1 | | 3/2001 | Boyer et al. |

* cited by examiner

Primary Examiner—Gene O. Crawford
(74) Attorney, Agent, or Firm—Thorp Reed & Armstrong LLP (57) ABSTRACT

The present invention is directed to a method of dispensing or administering medications which requires prompting the user for a reason if the user wants to dispense or intends to administer a medication that is not on the patient's medication profile. For example, a patient may be in severe discomfort, or some other condition exists, that requires dispensing and administration of a medication not approved by a pharmacist for the patient. The method prompts the user to supply a reason (exception) for the dispensing or administering that can be used to create an audit trail. The method may include identifying a patient, accessing a medication profile for the identified patient, selecting a medication for the identified patient, the selected medication not having been reviewed against the patient's medication profile, prompting the user to identify an exception, and reviewing the exception to determine its acceptability. If the exception is acceptable, access to a dispensing apparatus' storage compartment(s) for the purpose of dispensing the medication may be granted and a record of the dispensing event is created, or the healthcare giver may administer the medication and a record of the administration is created. If the exception is not acceptable, a record of the request to dispense or the request to administer is created. The method may further include transferring the override requests and override events to a database containing pharmacy orders. The requests, events, and orders may be sorted according to a predetermined criterion, and presented to a pharmacist for review.

26 Claims, 6 Drawing Sheets

OVERRIDE HAVING BUILT IN AUDIT TRAIL FOR MEDICATION DISPENSING AND ADMINISTERING SYSTEMS

CROSS-REFERENCE TO RELATED APPLICATIONS

The instant application is a continuation-in-part application of U.S. application Ser. No. 10/124,045 entitled Medication Dispensing Apparatus Override check and Communication System filed Apr. 16, 2002 and assigned to the same assignee as the present invention.

BACKGROUND OF THE INVENTION

A wide variety of apparatus are used in healthcare facilities for the dispensing and inventory of medications and medical supplies. For example, U.S. Pat. No. 5,520,450 discloses a supply station with an internal computer. The supply station is comprised of a cabinet having a plurality of lockable doors. Information is provided to a computer which unlocks the doors. The computer may be used to simultaneously and automatically update a patient's record, billing information and hospital inventory. The relevant data may be displayed on a display or printed on a sheet of paper by a printer connected to the computer. Other examples of computer controlled dispensing apparatus are found in U.S. Pat. No. 5,346,297, U.S. Pat. No. 5,905,653 and U.S. Pat. No. 5,745,366.

Such computer controlled dispensing apparatus have been developed in response to a number of problems existing in hospitals and other healthcare institutions. More particularly, computer controlled dispensing apparatus are operated according to programming that addresses problems such as the removal of medications by unauthorized personnel, dispensing the wrong medication for a patient, inaccurate record keeping, to name a few.

The AcuDose-Rx dispensing cabinet available from McKesson Automation Inc. of Pittsburgh, Pa. is an example of a computer controlled cabinet programmed to address the aforementioned problems. The user must first logon to the computer (thereby identifying who is removing medications). The user then identifies a patient and is presented with a list a medications that has been approved for administering to the identified patient (thereby addressing the problem of incorrect dispensing). Records are kept for each dispensing event thereby creating an audit trail.

To ensure the safe and accurate dispensing and administration of medications, a pharmacist reviews each prescription or medication order against that patient's medication profile and other relevant patient information to identify such items as therapeutic duplication in the patient's medication regimen; appropriateness of the drug, dose, frequency, and route of administration; medication allergies or sensitivities; potentially significant drug-drug, drug-food, drug-lab, and drug-disease interactions; contraindications to use; any organizational criteria for use; and other relevant medication-related issues or concerns. If a question or concern arises, the pharmacist contacts the person who prescribed the medication.

Many computer controlled dispensing apparatus have a "medication order profile interface" system that requires that all new medication orders for patients be entered into a pharmacy information system, where they are checked as discussed above. After the pharmacy information system completes the necessary clinical checks, data must be transmitted to the dispensing apparatus before the nurse is free to access the medication in the dispensing apparatus. That is done to ensure that medications are not dispensed and subsequently administered without a prior review by a pharmacist.

Problems can arise, however, when a pharmacist is not available to provide the necessary review. In many institutions, pharmacists are not available around the clock, although patients may be admitted at any time. Additionally, an emergency may arise or a doctor may write a STAT order. Under such circumstances, when a healthcare provider, typically a nurse, must retrieve medication from the dispensing apparatus, the patient may not be recognized by the dispensing apparatus, or the desired medication may not yet be approved for the patient. As a result, to enable a dispense to occur, the nurse must exit the normal dispensing routine by entering an override mode, emergency mode, or the like. Unfortunately, in such alternative modes, control is lost over why the dispensing operation is needed, for whom, and the like. That loss of control and information has been recognized by the Joint Commission on Accreditation of Healthcare Organizations (JCAHO). In its proposed medication use standards, JCAHO provides that when a pharmacist is not on the premises, nurses can administer any medication needed for the patient without a pharmacist's prior review if the healthcare institution has developed an alternative system for medication order review that minimizes the impact of skipping the pharmacist's review prior to administration. At a minimum, that must include the following: a retrospective review of the medication orders by the pharmacist as soon as a pharmacist is available; a review of the medication order by a qualified healthcare professional prior to administration of the medication for appropriateness against a database of information (e.g., drug interaction reference and drug profile); and an ongoing analysis and monitoring of the process for the incidence of medication errors as compared to the incidence of medication errors when the pharmacy is open. The need exists for a medication dispensing and administering apparatus that facilitates dispensing events in a controlled, traceable manner in situations where an event is requested for medication not approved for a patient.

SUMMARY OF THE INVENTION

The present invention is directed to a method of dispensing or administering medications which requires prompting the user for a reason if the user wants to dispense or intends to administer a medication that is not on the patient's medication profile. For example, a patient may be in severe discomfort, or some other condition exists, that requires dispensing and administration of a medication not approved by a pharmacist for the patient. The method prompts the user to supply a reason (exception) for the dispensing or administering that can be used to create an audit trail. The method may include identifying a patient, accessing a medication profile for the identified patient, selecting a medication for the identified patient, the selected medication not having been reviewed against the patient's medication profile, prompting the user to identify an exception, and reviewing the exception to determine its acceptability. If the exception is acceptable, access to a dispensing apparatus' storage compartment(s) for the purpose of dispensing the medication may be granted and a record of the dispensing event is created, or the healthcare giver may administer the medication and a record of the administration is created. If the exception is not acceptable, a record of the request to dispense or the request to administer is created. The method may further include transferring the override requests and override events to a database containing pharmacy orders. The requests, events, and orders may be sorted according to a predetermined criterion, and presented to a pharmacist for review.

The present invention prevents dispensing and warns against administering medications when the medication has not been approved for the patient and no acceptable reason exists for not waiting until a pharmacist can make the necessary review. If an acceptable reason exists for a dispensing/administering before the necessary review by a pharmacist has taken place, the present invention provides documentation and an audit trail of the reasons for the event. With electronic collection and distribution of events or requests for events, efficiencies and cost savings are enabled. Further, that information can be sent to centralized 24/7 pharmacies that provide after-hours services to institutions that are not staffed in off hours, thereby insuring compliance even with reduced hours and staff. Those advantages and benefits, and others, will be apparent from the description below.

BRIEF DESCRIPTION OF THE DRAWINGS

For the present invention to be easily understood and readily practiced, the present invention will now be described, for purposes of illustration and not limitation, in conjunction with the following figures, wherein.

DESCRIPTION OF THE INVENTION

Figure 1:
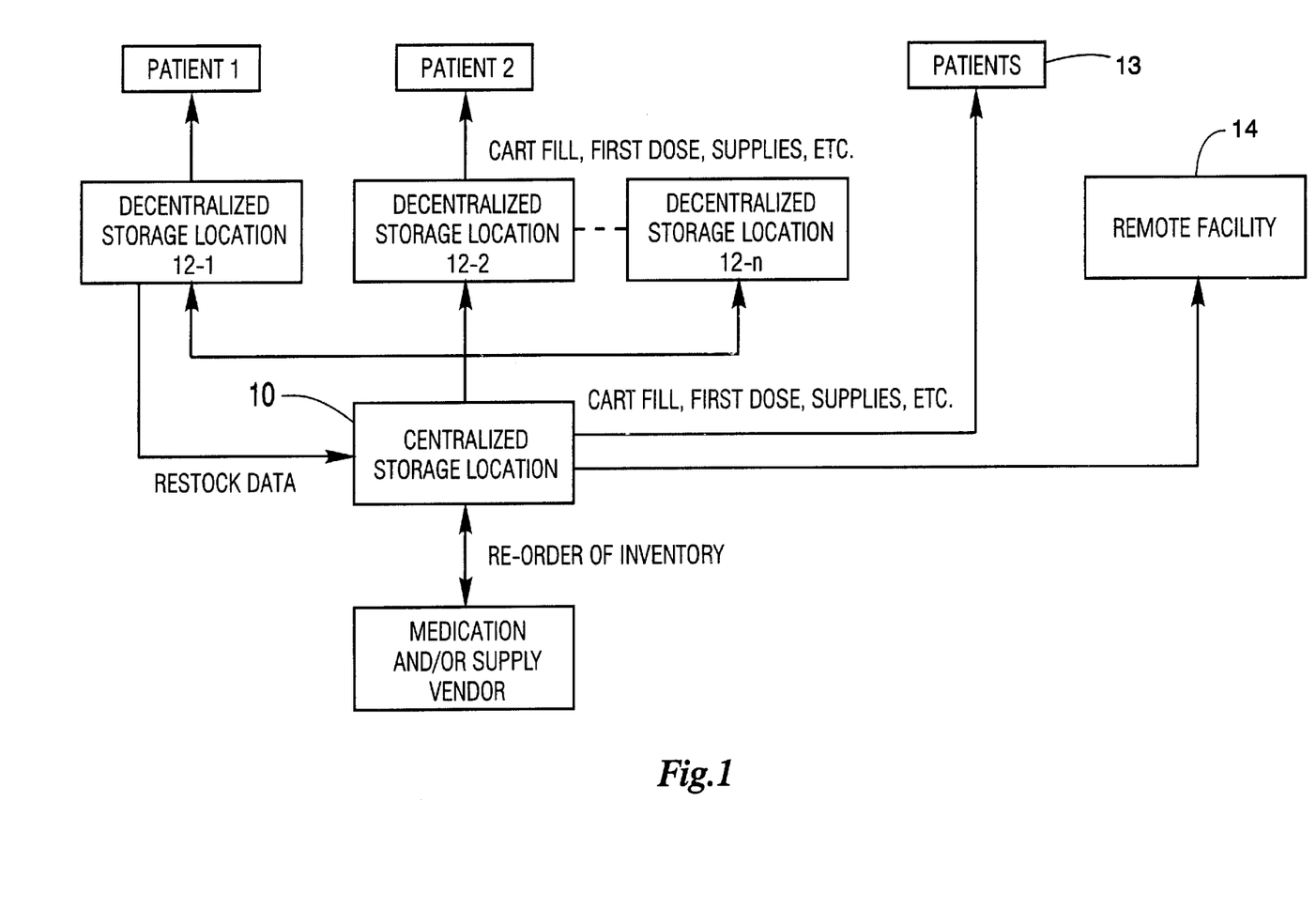
FIG. 1 is a diagram illustrating the relationship between a centralized storage location and, among other things, a plurality of storage locations.

FIG. 1 is a diagram illustrating the relationship between a centralized storage location 10 and various inventory destinations, including a plurality of decentralized storage locations 12-1, 12-2 through 12-n, patients 13, and a remote facility 14. Each of the decentralized storage locations 12-1 through 12-n is capable of dispensing items stored at the location. The items may include medications, controlled medical supplies, medical supplies or items of a nature consistent with the facility in which the system illustrated in FIG. 1 is located. Items may be dispensed directly from centralized storage location 10 to patients 13, or from the centralized storage location 10 to a remote facility 14. Data typically flows from the decentralized storage locations 12-1 through 12-n to the centralized storage location 10. In response to that data, items are typically moved from the central storage location 10 to the decentralized storage locations 12-1 through 12-n or to the remote facility 14 to restock such locations to either replenish dispensed items or to stock new items. Decentralized locations could include satellite pharmacies, computerized medication cabinets, stationary/mobile medication carts, nurse servers, remote hospital pharmacies, supply closets, supply cabinets, etc. Supplies can be reordered from distributors based on levels of stock in the centralized storage location 10.

Figure 2:
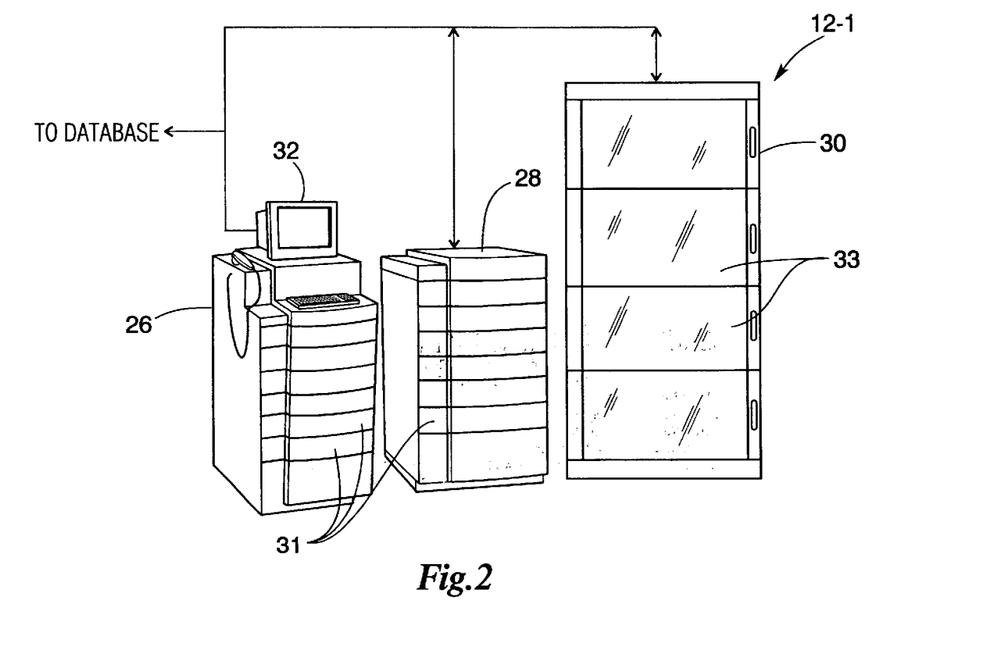
FIG. 2 is one example of apparatus located at a decentralized location implementing a closed system for performing dispensing operations.
Figure 3:
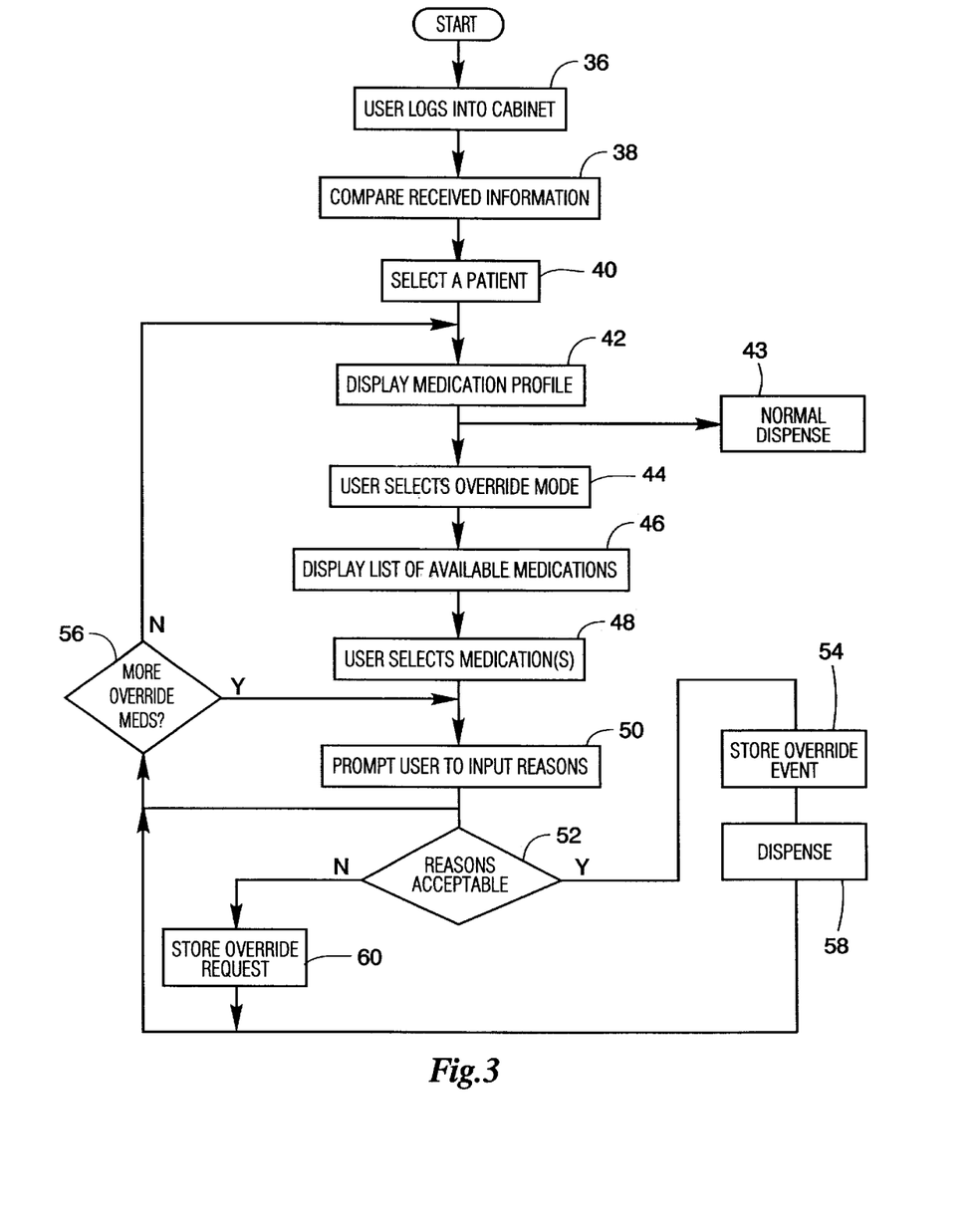
FIG. 3 is a flow chart illustrating a method of dispensing for a patient according to the present invention.

FIG. 2 illustrates one example of an apparatus that may be located at any of the decentralized locations 12-1 through 12-n. The apparatus illustrated in FIG. 3 is comprised of an AcuDose-Rx™ cabinet 26 and an AcuDose-Rx™ auxiliary cabinet 28 available from McKesson Automation Inc. A supply tower 30 is also illustrated. A control computer 32 controls the operation of the cabinet 26, auxiliary cabinet 28, and supply tower 30. The control computer 32 is also in communication with a central database (not shown). The reader will understand that the present invention is not limited to the AcuDose-Rx™ cabinet 26, but rather the method of the present invention may be implemented on any type of computer controlled dispensing apparatus.

Figure 5:
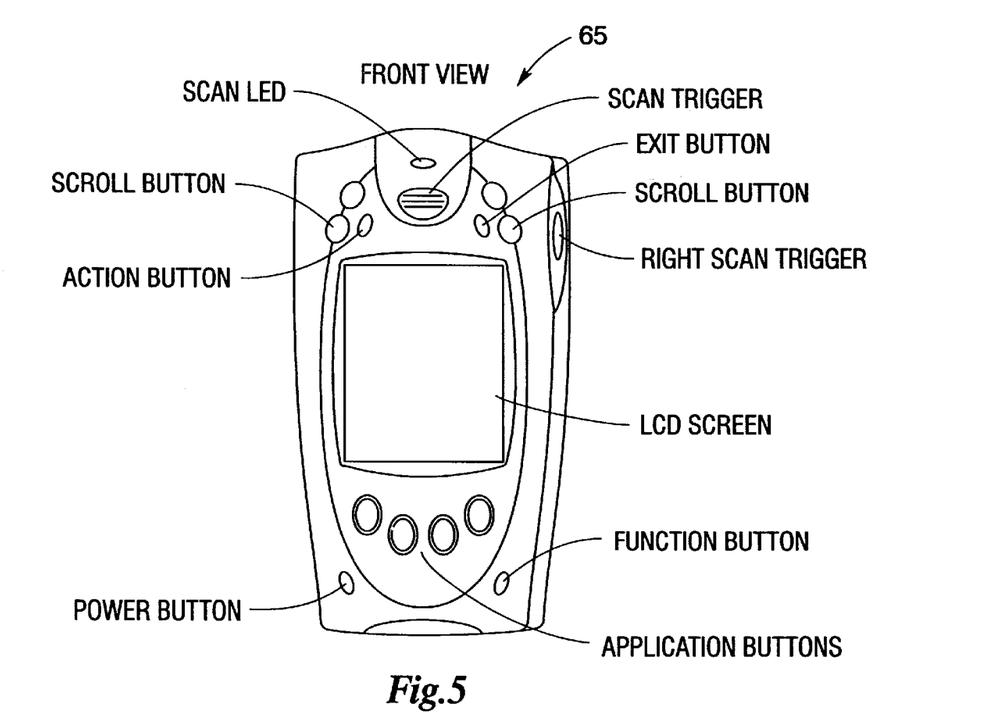
FIG. 5 is an illustration of a type of handheld scanner/administration device with which the present invention may be used.
Figure 6:
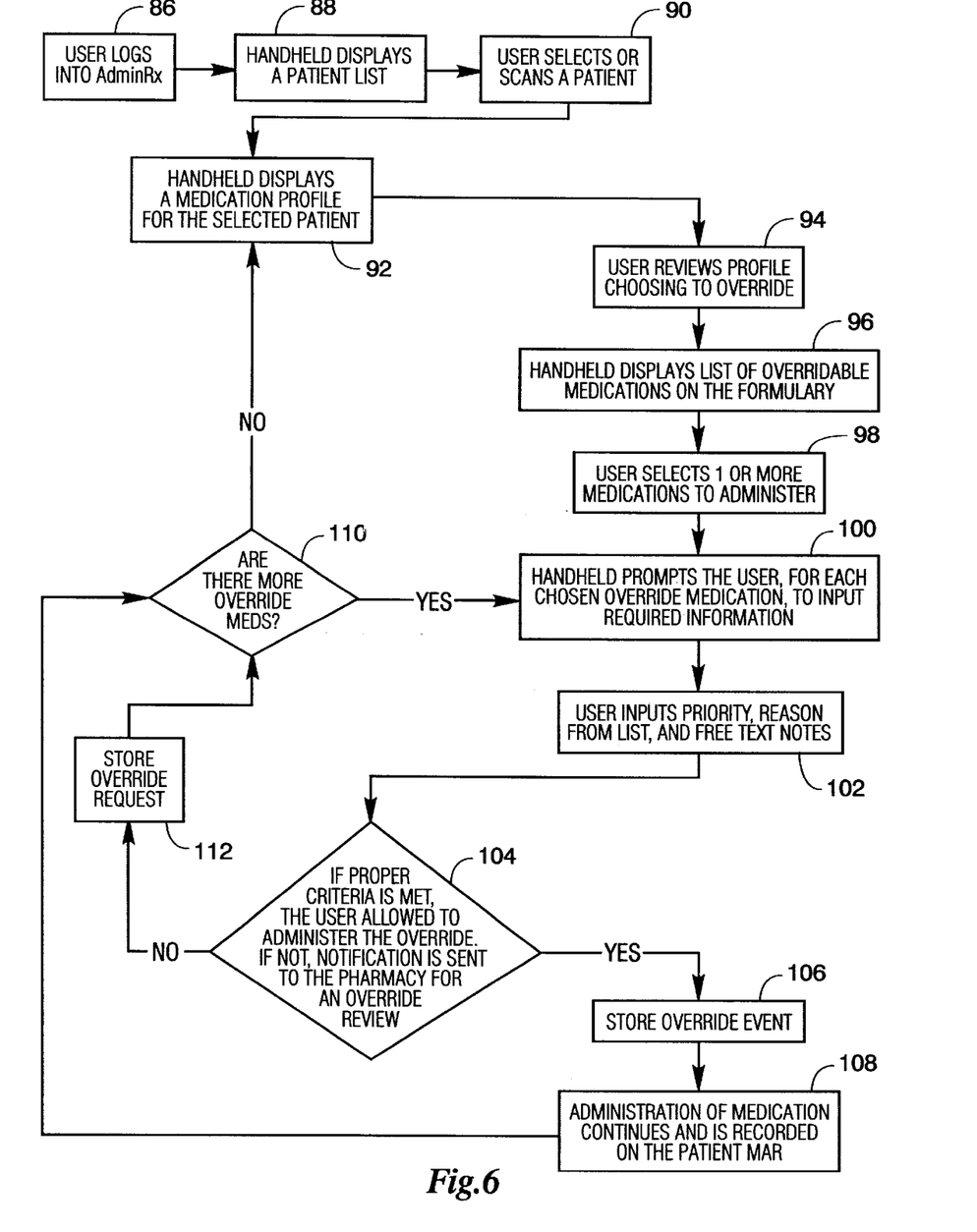
FIG. 6 is a flow chart illustrating a method of administering for a patient which may be used in conjunction with the device of FIG. 5.

Turning now to FIG. 6, a flow chart illustrating a method which may be practiced on the handheld device 65 illustrated in FIG. 5 is shown.*** To perform a dispensing operation a user logs onto the control computer 32 at step 36. In that manner, the computer receives information identifying the user. The user information is compared to stored information at step 38. At step 40 a patient is identified. The information could be entered on a keypad, either by name or by an ID number, the information could be scanned, selected from a pick list, or any other known method of entering the patient information. In that manner, the computer receives information identifying the patient.

At step 42 a medication profile for the patient is displayed. The display may include all of the medications which have been approved by a pharmacist for administration to the patient. For a normal dispensing event, not shown in detail but represented by the box 43, the user then selects from the displayed medications. However, if the medication has been ordered on a STAT or emergency basis, it may not be displayed at step 42. The user then selects at step 44 an override mode. The use of the phrase "override mode" is not intended to limit the present invention. In the vernacular of the AcuDose cabinet, when a user wishes to select a medication not in the patient's medication profile, the override mode is enabled. Sometimes a patient has not yet been admitted on the system, thus requiring creation of a patient record prior to proceeding. In those cases, the user is taken directly to the list of medications available for dispensing. Other cabinet manufacturers may use other terminology. The concept is that the user wishes to select a medication for dispensing which is not on the patient's medication profile or, in other words, the user wishes to dispense a medication prior to review by a pharmacist or other qualified healthcare provider, regardless of whether that is referred to as an override mode, an emergency mode, or any other phrase specific to a particular manufacturer.

At step 46, the control computer 32 displays a list of medications available for dispensing. The list could include all of the medications in the various cabinets, auxiliary cabinets, supply towers and the like under the control of the control computer 32, or some set of that list for which the particular user has authority to dispense. At step 48, the user selects the desired medication or medications. Selection could be via a touch screen, entry through a keypad, or any other known method of entering information for enabling the selection. In that manner, the control computer receives information identifying a medication to dispense. At step 50 the user is prompted to enter information. The information being entered may be variously described as an "exception" to the general rule that a medication cannot be dispensed unless the order has been reviewed by a pharmacist or the "reasons" why the dispense is necessary. There are two recognized exceptions for when an nurse can dispense prior to a pharmacists review, e.g. in the override mode. The first is a situation in which a physician or other qualified healthcare provider controls the ordering, dispensing and administration of the medication, such as in an operating room, endoscopy suite, or an emergency room. The second exception is for those emergencies when there is not sufficient time to obtain the necessary review. Those include STAT orders or those orders where the clinical status of the patient would be significantly compromised by the delay that would result from waiting for a pharmacist's review. Not all first orders meet these criteria.

Figure 4:
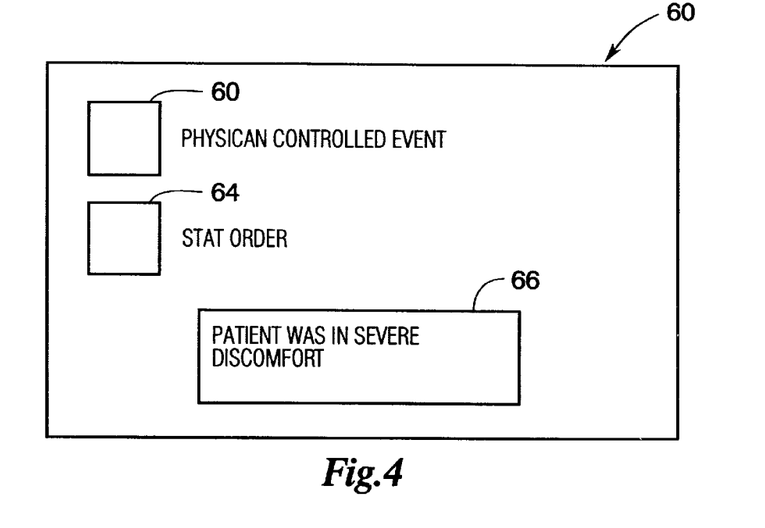
FIG. 4 is an exemplary screen illustrating one way of prompting a user for information.

An example of an exemplary screen 60 used to prompt the user to provide the required information is illustrated in FIG. 4. In FIG. 4, two exceptions acceptable to an organization such as JCAHO are illustrated: physician controlled dispensing 62 and STAT order 64. The curser may be placed in the appropriate box and a keystroke entered. However, the information may be input in any known way such as selecting a reason or exception from a pick list, or the like. The exceptions or reasons shown to the user may be hard coded by the manufacturer, soft coded to allow the user to create the text, or customizable hard code, where the user selects which exceptions from among numerous exceptions will be displayed, or any other known manner.

In addition to a listing of various exceptions a text box 66 may be provided. The text box may be used to record textual information which the nurse wishes to add to the record. In an alternative embodiment, the textbox may be used in place of a list. In that embodiment, the text in the text box is subjected to character recognition followed by a search for keywords to determine if the exception or reason for the dispense is adequate. A reason for dispensing each medication selected at step 48 must be provided at step 50.

At step 52, an evaluation is made to determine if the reasons input at step 50 are sufficient. For example, if one of the reasons is an exception recognized by a committee such as JCAHO, and the box 62, 64 next to that reason has been selected, then the process continues at step 54 where the "override" event is stored and a dispensing event takes place at step 58. It should be recognized that the analysis performed at step 52 will depend to a large degree on the type of information input at step 50. For example, if at step 50 the user's only options are to choose amongst acceptable exceptions, then perhaps the only analysis that needs to be performed at step 52 is whether one of the exceptions has been selected. If, however, at step 50 the user is prompted to select from a list of numerous exceptions, some of which are acceptable and some of which are not, it may be necessary at step 52 to determine if an acceptable exception has been selected. In yet another embodiment, where all that is provided is a text box, at step 52 it may be necessary to perform character recognition, and then perform an analysis upon the recognized characters to determine if the proper keywords or phrases have been used for a recognized exception. The present invention is not to be limited by the manner in which the user is prompted to input reasons at step 50 and the manner in which those reasons are evaluated at step 52.

It should also be noted that code may be provided for disabling steps 50 and 52. For example, in a hospital or other healthcare institution in which procedures are already in place to properly document dispenses in an "override" mode, the institution may choose to disable steps 50 and 52 and proceed directly to storage of the override event 54 and dispensing at step 58 as soon as the user selects the medications at step 48.

Assuming that the reasons were acceptable at step 52, as noted the override event is stored at step 54. Thereafter, a dispensing event occurs at step 58 and the process returns to step 56. If the reasons were unacceptable at step 52, the override request is stored at step 60 and the process continues with step 56.

After an override request has been stored at step 60, or a dispensing event has occurred at step 58, one important aspect from the healthcare institution's perspective is to have a pharmacist review either the override request or the override event as soon as possible. That may be implemented in at least two ways. First, the records of the override requests and override events may be printed, for example, at a pharmacy computer, or if an electronic pharmacy system is available, the records of the override requests and override events may be forwarded to the pharmacy system, as will be described in greater detail in conjunction with FIG. 7.

The previous paragraphs describe how a dispensing event for a patient may be performed in conjunction with a medication not listed on the patient's profile. A similar situation may arise when a medication which is not on a patient's profile is to be administered. The administration of medication may be controlled through the use of a scanner/administrating device 65 of the type illustrated in FIG. 5. Such devices are commercially available. An example of one such device is sold under the name AcuScan-Rx by McKesson Automation Inc. of Pittsburgh, Pa. The device 65 is capable of receiving information about a patient, for example through scanning a patient's bracelet, selecting a patient from a pick list, or entering patient ID information. The device 65 may include an RF transmitting device allowing the device 65 to be in real time communication with a database which may be located at the centralized location, hospital pharmacy, or other location. Other types of scanner/administrating devices may require docking in a base station before communicating with the database.

Turning now to FIG. 6, a flow chart illustrating a method which may be practiced on the handheld device 65 illustrated in FIG. 5 is shown. To perform an administering operation a user logs into the computer controlled handheld device 65 at step 86. In that manner, the computer (not shown) of the device 65 receives information identifying the user. The handheld device 65 displays a patient list at step 88. At step 90 a patient is identified. The information could be entered on a keypad, either by name or by an ID number, the information could be scanned, selected from a pick list, or any other known method of entering the patient information. In that manner, the computer of the handheld device 65 receives information identifying the patient.

At step 92 a medication profile for the patient is displayed. The display may include all of the medications which have been approved by a pharmacist for administration to the patient. For a normal administering event, not shown, the user then selects from the displayed medications. However, if the medication has been ordered on a STAT or emergency basis, it may not be displayed at step 92. The user then selects at step 94 an override mode. The use of the phrase "override mode" is not intended to limit the present invention. In the vernacular of an AcuScan Rx handheld device, when a user wishes to select a medication not in the patient's medication profile, the override mode is enabled. Sometimes a patient has not yet been admitted on the system, thus requiring creation of a patient record prior to proceeding. In those cases, the user is taken directly to the list of medications available for administering. Other manufacturers may use other terminology. The concept is that the user wishes to select a medication for administering which is not on the patient's medication profile or, in other words, the user wishes to administer a medication prior to review by a pharmacist or other qualified healthcare provider, regardless of whether that is referred to as an override mode, an emergency mode, or any other phrase specific to a particular manufacturer.

At step 96, the handheld device 65 displays a list of medications available for administering. The list could include all of the medications in the various cabinets, auxiliary cabinets, supply towers and the like in communication with the handheld device 65, or some set of that list for which the particular user has authority to administer. Typically, at this point, the healthcare worker has already dispensed or otherwise obtained the medication that is to be administered. At step 98, the user selects the desired medication or medications from the list. Selection could be via a touch screen, entry through a keypad, or any other known method of entering information for enabling the selection. In that manner, the handheld device 65 receives information identifying a medication to be administered.

At step the user is prompted to enter information. The information being entered at step 102 may be variously described as an "exception" to the general rule that a medication cannot be administered unless the order has been reviewed by a pharmacist or the "reasons" why the administering is necessary. There are two recognized exceptions for when an nurse can administer prior to a pharmacists review, e.g. in the override mode. The first is a situation in which a physician or other qualified healthcare provider controls the ordering, dispensing and administration of the medication, such as in an operating room, endoscopy suite, or an emergency room. The second exception is for those emergencies when there is not sufficient time to obtain the necessary review. Those include STAT orders or those orders where the clinical status of the patient would be significantly compromised by the delay that would result from waiting for a pharmacist's review. Not all first orders meet these criteria. The exemplary screen 60 illustrated in FIG. 4 and described in conjunction with the process of FIG. 3 may also be used in conjunction with the process of FIG. 6.

At step 104, an evaluation is made to determine if the reasons input at step 102 are sufficient. For example, if one of the reasons is an exception recognized by a committee such as JCAHO, and the box 62, 64 (see FIG. 4) next to that reason has been selected, then the process continues at step 106 where the "override" event is stored and an administering event takes place at step 108. It should be recognized that the analysis performed at step 104 will depend to a large degree on the type of information input at step 102. For example, if at step 102 the user's only options are to choose amongst acceptable exceptions, then perhaps the only analysis that needs to be performed at step 104 is whether one of the exceptions has been selected. If, however, at step the user is prompted to select from a list of numerous exceptions, some of which are acceptable and some of which are not, it may be necessary at step 104 to determine if an acceptable exception has been selected. In yet another embodiment, where all that is provided is a text box, at step 104 it may be necessary to perform character recognition, and then perform an analysis upon the recognized characters to determine if the proper keywords or phrases have been used for a recognized exception. The present invention is not to be limited by the manner in which the user is prompted at step and inputs reasons at step 102 and the manner in which those reasons are evaluated at step 104.

It should also be noted that code may be provided for disabling steps, 102 and 104. For example, in a hospital or other healthcare institution in which procedures are already in place to properly document administerings in an "override" mode, the institution may choose to disable steps, 102 and 104 and proceed directly to storage of the override event 106 and administering at step 108 as soon as the user selects the medications at step 98. In other circumstances, for example if computer controlled dispensing devices are used in a healthcare facility, it may not be necessary or desirable to duplicate the audit trial at the time of administering if an audit trial was created at the time of dispensing.

Assuming that the reasons were acceptable at step 104, as noted the override event is stored at step 106. Thereafter, an administering event occurs at step 108 and the process returns to step 110. If the reasons were unacceptable at step 104, the override request is stored at step 112 and the process continues with step 110.

After an override request has been stored at step 112, or an administering event has occurred at step 108, one important aspect from the healthcare institution's perspective is to have a pharmacist review either the override request or the override event as soon as possible. That may be implemented in at least two ways. First, the records of the override requests and override events may be printed, for example, at a pharmacy computer, or if an electronic pharmacy system is available, the records of the override requests and override events may be forwarded to the pharmacy system, as will be described in greater detail in conjunction with FIG. 7.

Figure 7:
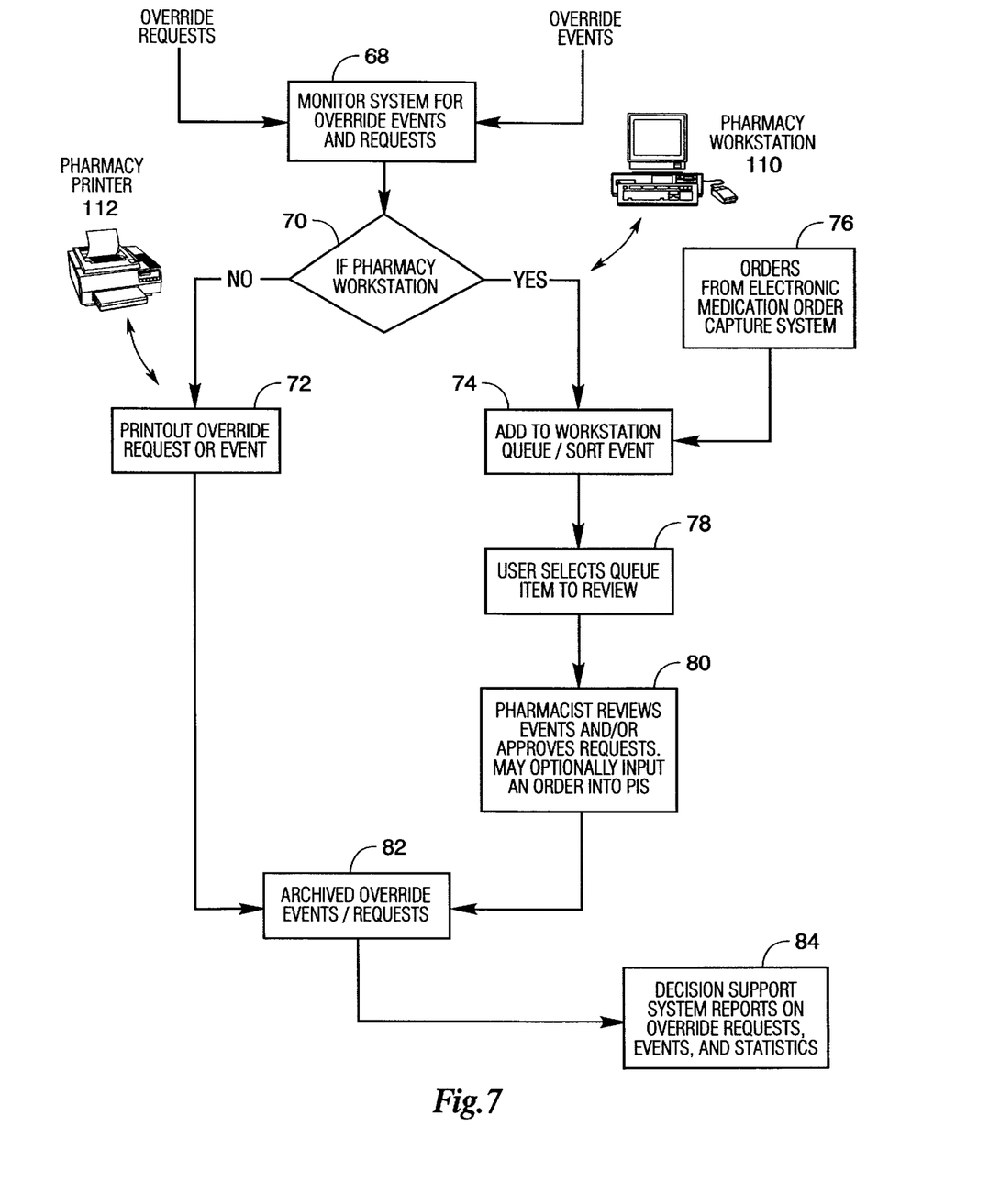
FIG. 7 is a flow chart illustrating a method of communicating and processing override events.

In FIG. 7, a flow chart illustrating another method according to the present invention is illustrated. In FIG. 7, records for each override request stored at step 60 in FIG. 3 or step 112 in FIG. 6, and records of each override event stored at step 54 in FIG. 3 and step 106 in FIG. 6, are monitored at step 68. A decision is made at step 70 if a pharmacy workstation 110 exists. If there is no pharmacy workstation 110, then the override requests and override events are printed at step 72, preferably at a pharmacy printer 112, so that they may be reviewed by a pharmacist as soon as practicable. If there is a pharmacy workstation 110, then the records representative of the override requests and override events are added to the workstation queue at step 74.

The workstation queue may be created, in the first instance, by commercially available products such as the Pyxis Connect product available from Pyxis Corporation or the MedDirect product available from McKesson Automation, Inc. as represented by block 76. The MedDirect product is an automated system for communicating medication orders and for managing documents. Using imaging technology, the MedDirect product delivers clear, scanned medication order images directly to the hospital pharmacy, where they can be viewed simultaneously with the pharmacy information system. Once the order is reviewed and approved by a pharmacist, it is entered in the pharmacy information system and made available for profile dispensing and administering by, for example, the AcuDose cabinet 26 (FIG. 2) or the AcuScan Rx handheld device (FIG. 5), respectively. At step 74, certain logic or rules may be applied to the queue to sort or reorder the queue. For example, records representative of override events may be placed at the front of the queue.

At step 78, the user selects a record from the queue to review. At step 80, a user, typically a pharmacist, will review the override events and/or approve override requests. The pharmacist may optionally input orders into a pharmacy information system. At step 82, the override requests and override events are archived for later review by a decision support system or the like as represented by step 84.

A hospital may received a type I recommendation from an organization such as JCAHO because nurses are accessing medication dispensing and administering apparatus for first doses of medication. Implementation of the present invention provides a hospital with evidence that policy and procedures are being adhered to, as well as providing an audit trail of all override activities associated with computer-controlled medication dispensing and administering apparatus.

Having the present invention integrated into computer-controlled medication dispensing and administering apparatus provides an electronic transfer of the information immediately, or based on a time delay, to a location where a pharmacist is available, thus creating efficiencies and cost savings. With electronic collection and distribution of the override information, that information can be sent to centralized 24/7 pharmacies that provide after-hours services to institutions that are not staffed in off hours, thereby insuring compliance even with reduced hours and staff. Electronic communications systems can be attached, such as cell phones, beepers, and e-mail to provide notification to pharmacists of the need to address override events and/or requests. More sophisticated wireless PDAs (personal digital assistants) can actually be connected to such systems, alerting pharmacists of the need to address override events and/or requests, allowing them to review the collected information, and providing approval transactions from remote locations.

Patient safety is ultimately enhanced when computer-controlled medication dispensing and administering apparatus incorporate the present invention so as to aid caregivers during overrides. Providing the means of enforcing and auditing hospital policy and procedures directly contributes to overall patient safety in compliance with JCAHO recommendations.

Many hospitals may have both systems in place, that is, computer controlled medication dispensing and administering apparatus. The caregiver may foreseeable have to go through the override process twice. That is, they may have to override at the dispensing cabinet and override again at the handheld device for administering. This may result in the creation of two records. Some institutions may choose to have two records. Other institutions may choose to suppress the second record. The choice to suppress a record may be an option of the handheld device 65 provided to the user at step in FIG. 6.

While the present invention has been described in conjunction with preferred embodiments thereof, those of ordinary skill in the art will recognize that many modifications and variations may be implemented while still falling within the scope of the present invention. Other types of dispensing and administrating devices may be used, and process steps may be substituted for those described in the preferred embodiment while remaining within the scope of the present invention. The description of presently preferred embodiments is not intended to limit the scope of the present invention, which is defined by the following claims.

What is claimed is:

1. A method, comprising:
   accessing a computer controlled apparatus;
   identifying a patient;
   accessing a medication for the identified patient, said selected medication not appearing on the patient's medication profile;
   prompting the user to identify an exception; and
   reviewing the exception to determine its acceptability.

2. The method of claim 1 wherein said prompting includes providing a pick list of exceptions.

3. The method of claim 1 wherein said prompting includes providing a text box.

4. The method of claim 1 additionally comprising one of administering and dispensing said selected medication if said review is positive and additionally comprising storing a record of said selecting if said review is negative.

5. The method of claim 4 additionally comprising suppressing said prompting, and wherein said selected medication is one of administered and dispensed.

6. The method of claim 4 additionally comprising printing one of a record of an administering event, a record of a dispensing event and a record of a selected event.

7. The method of claim 4 additionally comprising forwarding one of a record of an administering event, a record of a dispensing event and a record of a selecting event.

8. A method of controlling the administration of a medication to a patient when the medication does note appear in the patient's medication profile, comprising:
   logging onto a computer controlled dispensing device;
   identifying a patient;
   selecting a medication to administer in an override mode;
   receiving an exception from the user after a medication is selected; and
   when the exception is an approved exception, recording the administration of the medication to the patient.

9. The method of claim 8 wherein said receiving includes providing a pick list of exceptions.

10. The method of claim 8 additionally comprising providing a text box for entry of text.

11. The method of claim 8 additionally comprising suppressing said receiving, and wherein said recording the administration of the medication to the patient is performed without the need to receive an exception.

12. The method of claim 8 additionally comprising storing a request to administer when no exception is provided.

13. The method of claim 8 additionally comprising storing a request to administer when the exception is not an approved exception.

14. The method of claim 12 or 13 additionally comprising printing one of a record of an administering event and a record of the request to administer.

15. The method of claim 14 additionally comprising forwarding one of a record of an administering event and a record of the request to administer.

16. A computer readable medium encoded with a computer program which, when executed, performs a method comprising:
   receiving information identifying a user;
   comparing the received information to stored information about the user;
   receiving information identifying a patient;
   receiving information identifying a medication; and
   prompting the user to enter an exception when the medication does not appear on a list of approved medications for the patient.

17. The computer readable medium of claim 16 additionally comprising code which, when executed, performs the additional step of disabling the step of prompting the user.

18. A computer readable medium encoded with a computer program which, when executed, performs a method comprising:
   receiving information identifying a user;
   comparing the received information to stored information about the user;
   receiving information identifying a patient;

displaying a medication profile for the identified patient;

receiving information identifying a mode in which medications other than those listed on the profile may be selected;

displaying a list of medications available for selection;

receiving information identifying a selected medication;

prompting the user to enter an exception; and evaluating said exception.

19. The computer readable medium of claim 18 additionally comprising code which, when executed, performs the additional step of disabling the step of prompting the user.

20. A method, comprising:

transferring a plurality of non-dispensed based override requests and override events into a database of pharmacy orders.

21. The method of claim 20 additionally providing remote notification of the existence said requests and events.

22. The method of claim 20 additionally providing remote viewing of the said requests and events.

23. The method of claim 20 additionally comprising sorting said requests, events, and orders according to a predetermined criterion.

24. The method of claim 23 additionally comprising viewing said sorted requests, events and orders.

25. A method, comprising:

storing a plurality of non-dispensed based override requests and override events;

transferring said stored plurality of override requests and override events to a database of pharmacy orders;

presenting said plurality of override requests and override events for review.

26. The method of claim 22 wherein said plurality of override requests and override events are presented before said pharmacy orders are presented.

* * * * *

UNITED STATES PATENT AND TRADEMARK OFFICE
CERTIFICATE OF CORRECTION

PATENT NO. : 6,671,579 B2
DATED : December 30, 2003
INVENTOR(S) : Spano, Jr. et al.

It is certified that error appears in the above-identified patent and that said Letters Patent is hereby corrected as shown below:

Column 1,
Line 43, delete "a", second occurrence, and insert therefore -- of --.

Column 4,
Line 16, delete "***".
Line 66, delete "an" and insert therefore -- a --.
Line 67, delete "pharmacists" and insert therefore -- pharmacist's --.

Column 5,
Line 27, delete "textbook" and insert therefore -- text box --.

Column 7,
Lines 19, 51 and 61, following "step", insert -- 100 --.
Line 25, delete "an" and insert therefore -- a --.
Line 25, delete "pharmacists" and insert therefore -- pharmacist's --.
Line 65, following "steps", insert -- 100, --.

Column 8,
Line 1, following "steps", insert -- 100, --.
Line 66, delete "received" and insert therefore -- receive --.
Lines 6 and 7, delete "trial" and insert therefore -- trail --.

Column 9,
Lines 35 and 59, insert a hyphen between "computer" and "controlled".
Line 45, following "step", insert -- 100 --.

Column 10,
Line 17, delete "note" and insert therefore -- not --.

UNITED STATES PATENT AND TRADEMARK OFFICE
CERTIFICATE OF CORRECTION

PATENT NO. : 6,671,579 B2
DATED : December 30, 2003
INVENTOR(S) : Spano, Jr. et al.

It is certified that error appears in the above-identified patent and that said Letters Patent is hereby corrected as shown below:

Column 11,
Line 18, following "existence", insert -- of --.

Column 12,
Line 12, following "orders;", insert -- and --.

Signed and Sealed this

Twelfth Day of October, 2004

JON W. DUDAS
*Director of the United States Patent and Trademark Office*